United States Patent [19]

Caraway et al.

[11] 4,084,590
[45] Apr. 18, 1978

[54] STOMA DRAINAGE APPLIANCE

[75] Inventors: William Russell Caraway, Walnut, Calif.; Clarence Mark Falkingham, Largo, Fla.

[73] Assignee: Howmedica, Inc., New York, N.Y.

[21] Appl. No.: 605,553

[22] Filed: Aug. 18, 1975

[51] Int. Cl.² .......................... A61F 5/44; A61M 3/00
[52] U.S. Cl. .................................................. 128/283
[58] Field of Search ............... 128/283, 272, 272.3, 128/295, 275; 222/517, 498, 543, 525, 212, 213, 544, 481.5, 481, 211, 460, 462, 528, 529, 527; 215/321, 317

[56] References Cited

U.S. PATENT DOCUMENTS

| 2,496,175 | 1/1950 | Perry | 128/283 |
|---|---|---|---|
| 3,039,464 | 6/1962 | Galindo | 128/283 |
| 3,181,743 | 5/1965 | Libit et al. | 222/528 |
| 3,186,410 | 6/1965 | Buono | 128/275 |
| 3,189,252 | 6/1965 | Miller | 128/DIG. 24 |
| 3,227,332 | 1/1966 | Gowdy et al. | 222/494 X |
| 3,300,099 | 1/1967 | Marona | 222/529 |
| 3,618,606 | 11/1971 | Brown | 128/283 |
| 3,712,304 | 1/1973 | Marsan | 128/283 |
| 3,768,476 | 10/1973 | Raitto | 128/275 |
| 3,780,739 | 12/1973 | Frank | 128/283 |
| 3,826,394 | 7/1974 | Stull | 215/321 X |
| 3,841,332 | 10/1974 | Treacle | 128/283 |
| 3,888,236 | 6/1975 | Marx | 128/295 X |

FOREIGN PATENT DOCUMENTS

| 1,119,568 | 7/1968 | United Kingdom | 128/283 |
|---|---|---|---|
| 1,370,622 | 10/1974 | United Kingdom | 128/283 |

Primary Examiner—J. Reed Fisher
Attorney, Agent, or Firm—Pennie & Edmonds

[57] ABSTRACT

A stoma drainage appliance having a fluid collecting pouch constructed of sheets of flexible material with two internal sheets sealed together at spaced intervals to provide a valve across the center of the pouch precluding upward flow of fluid between the two internal sheets. There is at least one unsealed space between the seals located so as to provide a direct, straight path from an inlet opening of the upper section of the pouch to the lower section of the pouch. The stoma drainage appliance further includes an outlet spout connected at the lower section of the pouch. The spout has a tapered opening with an inlet neck section of oval cross-section and an outlet end section of circular cross-section. The spout is made of flexible material for clamping along the neck section to close the spout and includes a cap for attachment to the end section thereof. A tubular coupling member is provided for connecting to the spout and it has an opening of tapered construction to accommodate external conduits of varying size.

9 Claims, 9 Drawing Figures

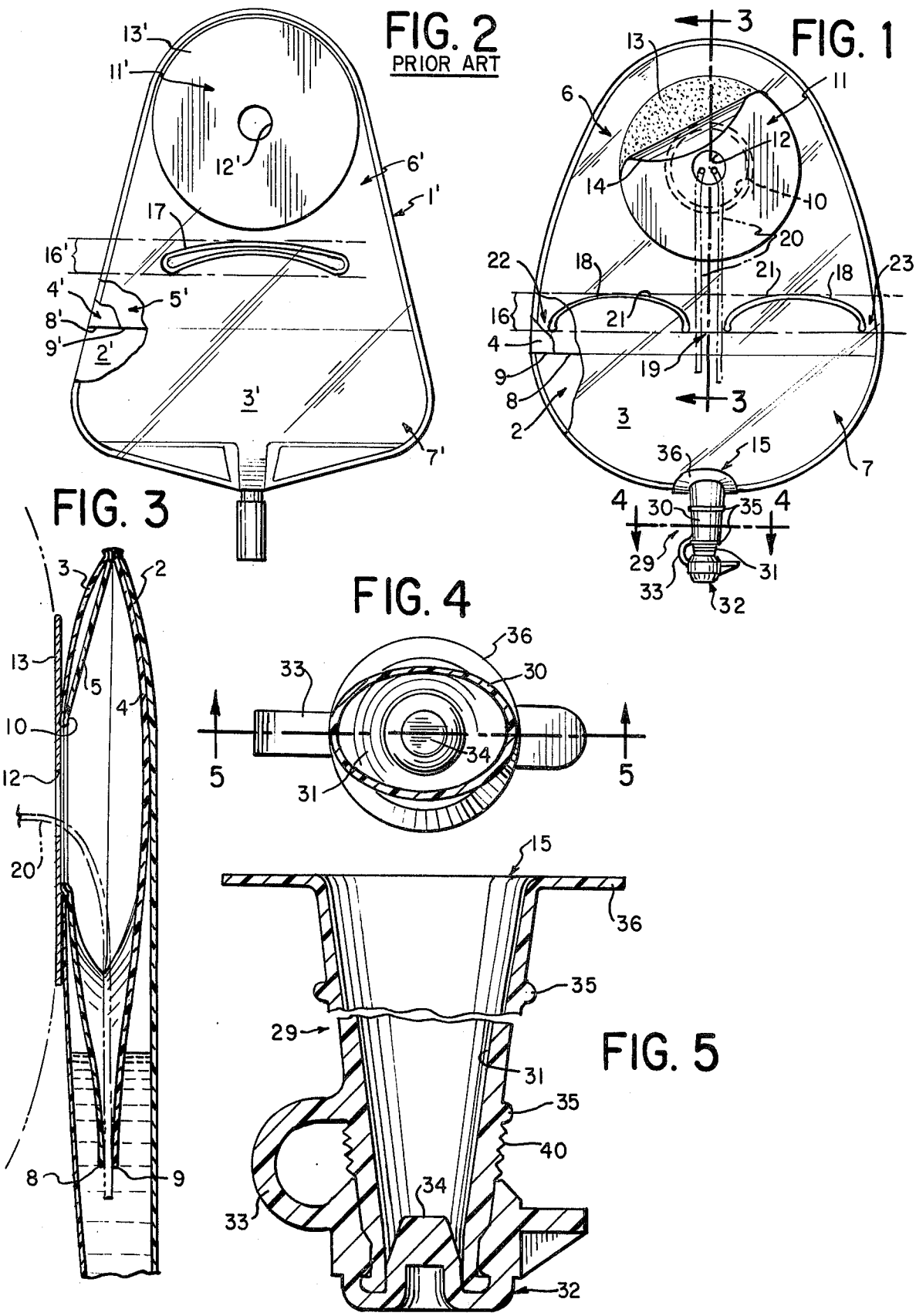

STOMA DRAINAGE APPLIANCE

BACKGROUND OF THE INVENTION

After ostomy surgical procedures, it is necessary for the patient to wear an appliance to collect the fluid discharged from the stoma which has been surgically formed at the abdominal wall of the patient. Such appliances commonly include a flexible pouch for collecting urine which is discharged from the stoma. There has been some difficulty with prior art devices in that the fluid as it collects within the pouch can splash or flow upwardly into the stoma as the patient moves about. This can cause skin irritation and/or infection.

In one type of drainage appliance constructed to avoid this problem, the pouch is formed of four superimposed layers of flexible sheet material. The two outside sheets form the outside of the pouch while the two inside sheets extend only across the upper section of the pouch. The sheets are all sealed together about their periphery to form the pouch and an inlet opening is provided in the upper section to provide communication with the space between the inside sheets. Drainage fluid from the stoma is received through this inlet opening and collects in the lower section of the pouch. To deter backward splashing or flow of fluid to the upper section of the pouch, the two internal sheets are sealed along a zone spaced from and extending generally along their lower edges, these edges extending across the center of the pouch. The sealing provides the necessary mechanism for permitting the lower edges of the inner sheets to function as a type of flutter valve which normally remains closed as fluid in the lower section of the pouch is collected and the walls thereof expanded.

Drainage appliances having the pouch construction as described above are generally useful in preventing backflow of fluid. However, the sealed construction of the inner sheets produces a barrier structure which has certain disadvantages. For example, immediately after an ostomy surgical procedure, it is normal post-operative practice to use drain tubes called stints while the stoma is healing. These tubes are inserted at their one ends into the stoma and the other ends are passed through the inlet opening in the pouch and down into the lower section of the pouch. With the sealed construction of the inner sheets, the drain tubes or stints must be snaked around the sealed area to reach the lower section of the pouch. These drain tubes are normally thin walled in construction and small in diameter. They can thus be readily kinked or squeezed closed by running into the sealed zone; and extreme care must be taken in directing the drain tubes into the pouch and in making sure that once in position they have not been damaged to the extent of restricting or precluding flow therethrough.

In addition to the above, prior art drainage appliances include an output spout and valve structure which presents problems in the area of clogging as the pouch is periodically emptied. Generally, the prior art outlet structures used with drainage appliances include a spout stem of rigid tubular construction having an opening therethrough of uniform circular cross-section. The spout stem is attached at one end to the lower section of the drainage appliance and a removable valve cap is provided for closing the outlet end of the spout. The spout and valve structure of this device has the disadvantage that is can become clogged during emptying due to the presence of mucous in the urine. This is especially so if the spout further includes any center support in the passageway. With this construction, it is also difficult to remove the cap from the spout and empty the pouch with assurance that this is neatly accomplished. Once the cap is removed and even when it is only partially removed, fluid starts to drain and there is no mechanical way of controlling it.

One final limitation of the present spout and valve structure is its ability to accommodate or be attached to external drainage conduits of varying construction. Attachment of the drainage appliances to external drains may, for example, be advantageous for night drainage or where the pouch is used in connection with a leg bag for wheel chair patients. External drain collection units of different manufacturers have different conduit constructions. Therefore, depending on which manufacturers' unit is used, it is generally necessary to provide a specially designed adapter to connect the unit to the spout of the pouch.

SUMMARY OF THE INVENTION

The stoma drainage appliance of the present invention avoids the problems and disadvantages of the prior art. In particular, the sealing of the inner sheets of the pouch to provide the valve function is effected by spaced seal lines extending along the lower edges of the inner sheets with at least one unsealed space positioned to provide a direct path between the inlet opening in the upper section of the pouch and the fluid collection area in the lower section of the pouch. With this construction, the post-operative use of drain tubes or stints is easily accomplished without damage to them. To further facilitate the direct passage of the tubes between the seal lines, these lines are provided with guiding surfaces for directing the tubes in the right direction.

As for the spout of the present invention, it is made of flexible material with a tapered oval shaped neck section. This section is adapted to be clamped together between the patient's fingers to seal the spout before the cap at the end is removed. This assures that discharge through the spout is controlled and not begun until the cap is completely removed.

The appliance of the present invention is also provided with a coupling member for permitting attachment of the drainage appliance to external collection units of different construction. The coupling member can be readily attached to the spout in a sealed relation; and for this purpose in the preferred embodiment both the coupling member and spout are made of the same vinyl plastic material with the same durometer hardness. Both the coupling member and spout also include striations or mating ridges which assure proper leakproof connection to each other. Finally, the coupling member is tubular in construction with the opening through it being of variable diameter to accommodate external drain conduits of varying constructions.

DESCRIPTION OF THE DRAWINGS

FIG. 1 is a plan view of the stoma drainage appliance of the present invention;

FIG. 2 is a plan view of a prior art construction of a stoma drainage appliance;

FIG. 3 is a cross-sectional view taken along the lines 3—3 of FIG. 1;

FIG. 4 is a cross-sectional view taken along the lines 4—4 of FIG. 3;

FIG. 5 is a cross-sectional view taken along the lines 5—5 of FIG. 4 showing the cross-sectional shape of the spout;

DETAILED DESCRIPTION OF THE PREFERRED EMBODIMENT

Figure 6:
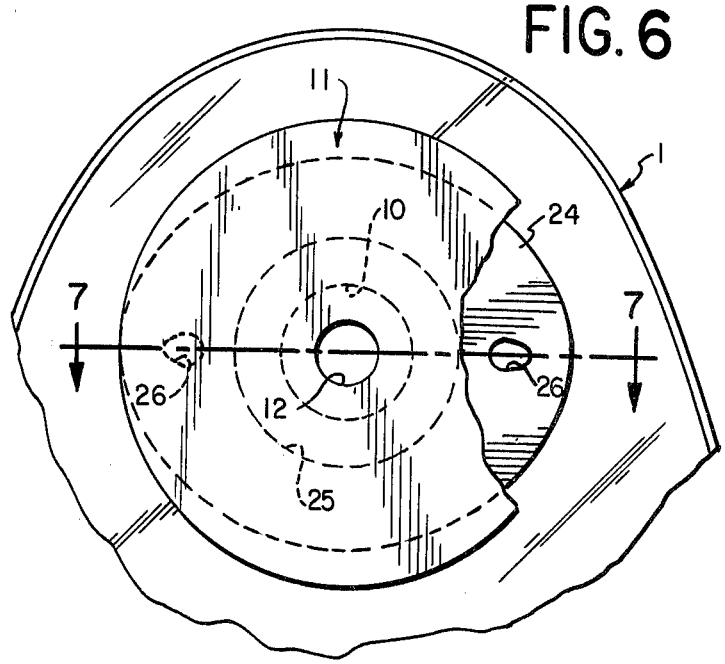
FIG. 6 is a partial view of the appliance of FIG. 2 showing a modified embodiment thereof.
Figure 7:
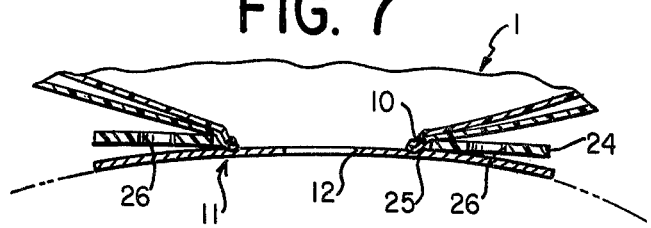
FIG. 7 is a cross-sectional view taken along the lines 7—7 of FIG. 6.

FIGS. 1 and 3 show the general construction of the drainage appliance constructed according to the teachings of the present invention. Certain basic features of this appliance are similar to those of prior art devices such as shown in FIG. 2. Accordingly, like reference numerals followed by the suffix prime are used in FIG. 2 to identify these similar parts.

Generally, the appliance includes a pouch 1 comprised of four superimposed layers of flexible material. These layers include two outside sheets 2 and 3 and two inside sheets 4 and 5. The sheets are sealed together along their peripheral edges to form the pouch. In the preferred embodiment, the flexible material is vinyl plastic having a thickness of about 3 to 10 mils and the sheets are sealed together by radio-frequency techniques.

The pouch is divided into an upper section 6 and lower section 7 and the sections are defined by having the two inside sheets 4 and 5 terminate midway between the top and bottom of the pouch. The lower edges of the inside sheets shown at 8 and 9 extend from one peripheral side edge of the pouch to the other. With this construction, the upper section 6 of the pouch is formed by all four sheets while the lower section 7 is defined by extensions of the outside sheets 2 and 3.

An inlet opening 10 is provided in the upper section of the pouch and communicates with the space between the two inside sheets. Drainage fluid from the stoma is received through the opening. An adhesive backed flexible and circular disc 11 is sealed at its center around the inlet opening 10. This disc also has a central opening 12 overlying the opening 10. As shown in FIG. 3, the opening 12 is smaller in diameter than the opening 10. Its size may be enlarged up to the size of the opening 10 to accommodte stomas of larger size. The disc 11 has a peripheral section 13 with the adhesive backed side facing away from the pouch. A relese paper 14 is removably attached to the adhesive backed side. Upon removal of the release paper, the disc is adapted to be adhered to the body of the individual around the stoma for attaching the appliance to the patient.

In the lower section of the pouch, an outlet opening generally designated at 15 is provided. This outlet opening communicates with the space between the two outside sheets for draining fluid collected in the bottom of the pouch. A spout and valve structure is provided for the outlet opening and will be described in more detail below.

In order to preclude or deter fluid collected in the lower section of the pouch from splashing or passing upwardly between the two inside sheets 4 and 5 and toward the inlet opening 10, these inside sheets are partially sealed together and to the outside sheets between the inlet opening 10 and their lower edges. This sealing is effected along a zone, designated by the dash lines 16, which is spaced from and extends generally along the edges 8 and 9 of the inside sheets. The sealing of the inside sheets in this manner provides the necessary mechanism to enable their edges to function as a type of flutter valve. With this construction, these edges tend to close and stay closed as the lower section of the pouch expands with collected fluid. Thus, as the patient moves about, such collected fluid will not flow backwardly to the stoma to cause irritation or infection.

The construction of the drainage appliance as so far described is the same as the prior art device of FIG. 2. In accordance with the teachings of the present invention, the construction and location of the sealing means of the present invention differs from that of the prior art device. In particular, FIG. 2 shows the prior art device as including one sealing line 17 of curved configuration disposed centrally between the peripheral side edges of the pouch and directly below the inlet opening 10'. With applicants' improved construction, the sealing line 17 of the prior art is replaced by a plurality of spaced seal lines 18 uniting the two inside sheets to each other and to the adjacent outside sheets. Between each of the seal lines an unsealed space is provided. With the preferred construction, two seal lines 18 are provided and a single unsealed space 19 is centrally located below the inlet opening 10 to provide a direct path between the inlet opening 10 and the lower section 7 of the pouch. This direct path accommodates the unobstructed passage of drain tubes or stints 20 from the stoma, through the inlet opening 10, through the unsealed space 19 and into the lower section of the pouch while following a generally straight line.

To further facilitate passage of the drain tubes through the unsealed space 19, the seal lines 18 are constructed with arcuate configurations so that they converge toward each other in a downward direction on each side of the space 19. As shown in FIG. 1, these arcuate seal lines have their concave sides facing generally downwardly toward the lower section of the pouch and their convex sides facing upwardly to define guiding surfaces 21 along which the drain tubes can slide as they are directed toward the lower section of the pouch. The drain tubes 20 are quite small in diameter and a plurality of tubes may be accommodated through the space 19. The lower edges 8 and 9 of the inside sheets will cling closely around the tubes 20 as the sheets function as a valve.

In the prior art construction shown in FIG. 2, any use of drain tubes requires snaking of the tubes around the seal line 17. Usually, the drain tubes will first strike the seal line 17 and then bend to the outside until striking the peripheral side of the pouch. It is then necessary for the tube to further bend in a downward direction to enter the lower section of the pouch. As best, initial insertion of a drain tube in a direction beyond the end of the seal line 17 will still cause it to engage the peripheral side edge of the pouch, and thus bend, before passing beyond the lower edges 8',9' of the inside sheets and entering the lower section 3' of the pouch. As discussed above, this presents disadvantages in possibly closing or retricting flow through the tubes. With the spaced seal line construction of the present invention, these problems are avoided.

Although drain tubes are customarily used immediately after ostomy surgery, they are not permanently required. As soon as the stoma has healed, they are no longer necessary and the patient may simply use the appliance in his day to day activity without tube connections. In accordance with the teachings of the present invention, the pouch of the appliance is constructed to accommodate undirected flow of fluid from the inlet opening 10 and into the lower section 6 of the pouch. For this purpose, the pair of sealing lines 18 is not only spaced centrally at 19 but each seal line is spaced from the peripheral side edge of the pouch as shown at 22 and 23 to provide further paths between the inlet opening and the lower section of the pouch.

As an example of a preferred construction of a drainage appliance having the features described above, the following is given. With a pouch having a height of about 8 inches and a width of about 6 inches, the arcuate guiding surfaces 21 extend a lateral distance across the pouch of about 2 inches and a vertical distance of about ⅜ of an inch as measured along a straight line perpendicular to the edges 8,9 of the inside sheets. They also terminate about ½ inch above these edges 8,9. The central space 19 separating the seal lines is about ⅜ of an inch while the side spaces are about ½ inch in width. Finally, the inlet opening is about 2½ inches above the edges 8,9 of the inside sheets.

The above dimensions are given only as an example and it is within the scope of the invention to change these dimensions provided the basic features of the pouch construction are retained. For example, the arcuate seal lines 18, and thus the arcuate guiding surfaces 21, can be formed on a radius ranging from about 1 to 3 inches. They may also extend laterally of the pouch within the range from about 1 to 2½ inches and their vertical extent may range from ½ to 1¼ inches as measured in a direction perpendicular to the edges 8,9 of the inside sheets. With seal lines formed on a radius of curvature of 1¼ inches and extended to form semicircular lines, their vertical extent will thus be 1¼ inches while their lateral extent will be 2½ inches. In addition to the modification of the contour of the seal lines, their spacing from each other and from the side walls may be varied within limits. The center space may vary from ½ to 1 inch while the side spaces between the seal lines and the sides of the pouch may vary from ¼ of an inch to ¾ of an inch. Also, although in the preferred construction, two spaced seal lines are shown, it is within the scope of the present invention to provide more than a pair of seal lines. Where this is done a plurality of unsealed spaced between the seal lines can be provided with each such unsealed space providing a direct, straight path from the unsealed opening 10 to the lower section 6 of the pouch for accommodating drain tubes.

FIG. 6 shows a modified embodiment of the present invention wherein additional means is provided for attaching the drainage appliance to the patient. More particularly, a flat ring shaped belt attaching member 24 is shown. This member is disposed in position between the pouch 1 and the circular disc 11. In accordance with the teachings of the present invention, the belt attaching member is removably attached to the drainage appliance; and for this purpose, the member includes a central opening 25. Through this opening, the flexible material of the pouch or that of the disc itself may be drawn to position the member as shown in FIG. 6. Locating the belt attaching member in this manner spaces the edge of the opening 25 radially outwardly of the opening 10 through the upper section of the pouch. The belt attaching member is generally stiff in construction and disposing the edge of the opening 25 at a location isolated from the opening 10 precludes this edge from contacting and thus irritating the stoma. The belt attaching member is adapted to be used together with the adhesive backed disc to more securely attach the appliance to the patient. Holes 26 are provided in the belt attaching members for attaching a support belt thereto.

Figure 8:
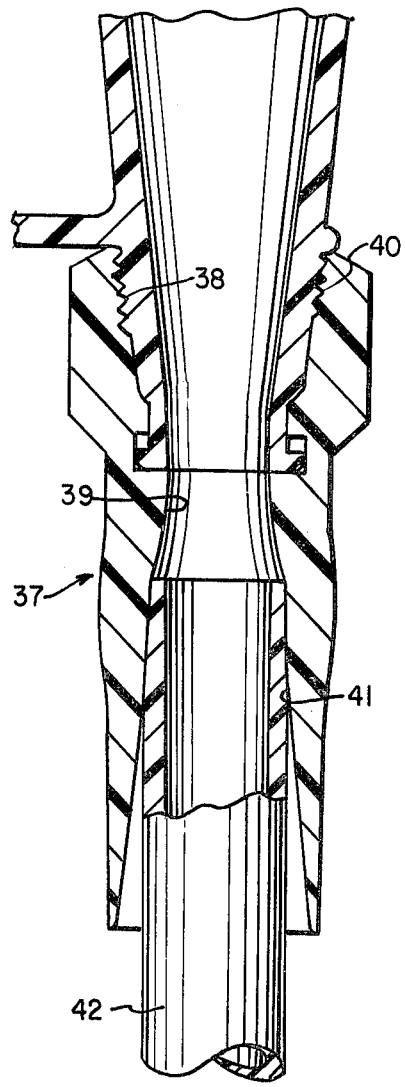
FIG. 8 is a cross-sectional view similar to FIG. 7 showing another modified embodiment of the invention.

FIG. 8 shows a further embodiment of the present invention. Here, the flexible circular disc for attaching the appliance to the patient is constructed of foam material 27 rather than of the flexible sheet material of the construction shown in FIG. 1. As with the construction of FIG. 1, however, the disc is provided with an adhesive side which is covered with removable release paper 28. The foam construction of FIG. 8 may be used in more sensitive situations to further assure a minimum of irritation to the patient.

The drainage appliance of the present invention includes an outlet spout 29 which is fixed to the lower section of the pouch at the outlet opening 15. The outlet spout is made of flexible vinyl plastic material and is constructed with an inlet neck section 30 and an outlet end section 31. As shown in FIGS. 4 and 5, the inlet neck section is oval in cross-section and has a tapered opening 31 extending therethrough.

In the presently preferred construction, the vinyl plastic from which the spout is made has a durometer hardness of between 65 and 75. The neck section of the spout is constructed with a thickness of about 0.078 inch and a median outside diameter of about 0.5 inch. The neck section of the spout is also provided with a pair of spaced circumferentially extending demarcation ridges 35. These ridges provide a visual indication to the patient that the neck portion of the spout is to be squeezed between the ridges to effect clamping and sealing of the spout. This construction of the spout permits easy finger clamping of the neck section to completely close the spout. This is desirable so as to permit proper control of the spout when emptying the drainage appliance.

As shown in FIG. 5, the outlet end of the spout includes a valve cap 32. The cap is formed integrally with the spout and connected thereto by a lanyard 33. An internal plug 34 is provided in the cap for insertion into the spout opening upon securing the cap to the spout. This type of construction permits the spout and cap to be made of flexible plastic and still provide an adequate seal. The plug 34 supports the wall of the spout opening so that the latter is properly sealed within the cap. The resiliency of the lanyard will automatically swing the cap out of the path of the spout so that the patient can release the clamping pressure on the neck section to empty the appliance in a neat manner.

The spout is constructed by a separate molding operation with an integrally formed and outwardly directed flange 36 at the inlet end thereof. This flange is provided for attaching the spout to the pouch of the drainage appliance. The attachment is effected by radio-frequency sealing and for this purpose, the flange 36 has a thickness no more than three or four times that of the pouch material. For example, with the pouch material having a thickness of 3 to 10 mils, the flange of the spout may range between about 0.010 and 0.020 inch. The vinyl plastic material of the spout is compatible with the vinyl plastic of the pouch for permitting this radio-frequency sealing.

A disadvantage of the prior art spout construction, as for example shown in FIG. 2, is that the spout is constructed with an opening of uniform cross-section. In some prior art constructions, the spout even includes center support structure for providing more rigidity to the spout. Since urine contains mucous, this type of prior art construction tends to become blocked. With the present tapered construction of the spout and with the unobstructed opening therethrough, this problem is avoided entirely and complete drainage of the appliance can be quickly effected.

Figure 9:
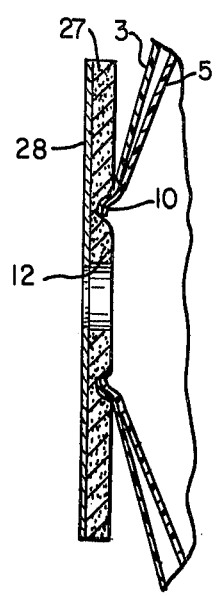
FIG. 9 is a cross-sectional view showing the construction of the coupling member of the present invention.

In some situations, it is necessary or desirable to connect the drainage appliance to an external collection unit. For example, during the night such a connection may be desirable. To effect this connection, the cap 32 is removed from the spout and a tubular coupling member shown at 37 in FIG. 9 is connected. This member is formed of the same vinyl plastic material as the spout with the same durometer hardness. As shown in FIG. 9, the coupling member has an internally striated or ribbed section 38 extending circumferentially around the opening 39 through the coupling member. This ribbed section is adapted to mate with a similar externally ribbed section 40 formed on the outlet end of the spout. In addition, the coupling member at its ribbed end is constructed of a thickness sufficient to make it relatively rigid as compared to the spout. This construction facilitates connection of the coupling member to the spout by simply pushing it on. Also, the ribbed section provides a friction fit of the coupling member to the spout for a fluid tight connection therewith.

The free end of the coupling member is adapted to be connected to external conduits of a fluid collection unit. In the preferred embodiment and for purposes of accommodating external conduits of different sizes, the opening through the coupling member tapers in cross-section as measured in the direction extending toward the free end thereof. This tapered construction is shown at 41. With this taper and with the flexible nature of the coupling member, insertion of an external conduit 42 having the size and tapered construction as shown in FIG. 9 will at some point intermediate the ends of the tapered section 41 effect a frictional sealed engagement in the coupling member. It will be appreciated that external conduits of different diameters will effect the same type of sealing as shown in FIG. 9. Thus, the coupling member can accommodate coupling to drainage units of different manufacture.

As an example of a presently preferred construction of the coupling member, it is constructed with a total length of about 1 9/16 inches and an outside diameter at its ribbed end of about 11/16 of an inch. The tapered opening through the coupling member extends for about 1 inch and is formed with a taper angle of about 5°. The median diameter of the opening is about 0.320 inch while the minimum diameter is the same as the spout opening and measures 0.218 inch.

We claim:

1. In a stoma drainage appliance having a pouch with upper and lower sections, the upper section being constructed of four superimposed layers of flexible material defined by two outside sheets and two inside sheets, and the lower section being constructed of two, superimposed layers of flexible material defined by extensions of said outside sheets, all of said layers being sealed to each other about their periphery to form said pouch, the lower edges of the two inside sheets extending freely across the pouch from one peripheral side edge to the other, an inlet opening in the upper section of the pouch communicating with the space between the two inside sheets and through which drainage fluid from the stoma is received, an outlet opening in the lower section of the pouch communicating with the space between the two outside sheets for draining collected fluid from said pouch, and sealing means disposed between said inlet opening and the lower edges of the two inside sheets for sealing said sheets together along a zone spaced from and extending generally along the lower edges to enable said lower edges to function as a valve deterring fluid collected in said lower section from flowing in an upward direction between said two inner sheets and into said upper section, the improvement wherein:
 (a) said sealing means is defined by two spaced arcuately shaped seal lines disposed along said zone with the concave sides facing away from said inlet opening and with an unsealed space between the seal lines and an unsealed space between each seal line and the peripheral side edges of the pouch;
 (b) the unsealed space between the seal lines is centrally located between the sides of the pouch directly below said inlet opening to provide a direct path between said inlet opening and the lower section of the pouch for passage of drain tubes entering said inlet opening, the convex sides of said seal lines defining arcuate guiding surfaces for guiding the drain tubes entering said inlet opening in a generally straight path through said space and into the lower section of the pouch; and
 (c) the seal lines unite the two inside sheets to each other and to the adjacent outside sheets.

2. The appliance of claim 1 wherein:
 (a) the centrally located unsealed space separates the seal lines by a distance between about ½ to 1 inch.

3. The appliance of claim 2 wherein:
 (a) the arcuate guiding surfaces each have a radius of between about 1 and 2½ inches.

4. The appliance of claim 3 wherein:
 (a) the arcuate guiding surfaces extend between about ½ to 1¼ inches as measured along a straight line in a direction perpendicular to the free edges of the inside sheets.

5. In a stoma drainage appliance having a pouch with upper and lower section, the upper section being constructed of four superimposed layers of flexible material defined by two outside sheets and two inside sheets, and the lower section being constructed of two, superimposed layers of flexible material defined by extensions of said outside sheets, all of said layers being sealed to each other about their periphery to form said pouch, the lower edges of the two inside sheets extending freely across the pouch from one peripheral side edge to the other, an inlet opening in the upper section of the pouch communicating with the space between the two inside sheets and through which drainage fluid from the stoma is received, an outlet opening in the lower section of the pouch communicating with the space between the two outside sheets for draining collected fluid from said pouch, and sealing means disposed between said inlet opening and the lower edges of the two inside sheets for sealing said sheets together along a zone spaced from and extending generally along the lower edges to enable said lower edges to function as a valve deterring fluid collected in said lower section from flowing in an upward direction between said two inner sheets and into said upper section, the improvement wherein:
 (a) said sealing means is defined by at least two seal lines disposed along said zone with an unsealed space between each seal line;

(b) at least one unsealed space is positioned to provide a direct path between said inlet opening and the lower section of the pouch for passage of drain tubes entering said inlet opening in a generally straight path into the lower section of the pouch;

(c) an outlet spout is connected to said outlet opening, said spout being flexible in construction and having:
(1) an inlet neck section, and
(2) an outlet end section having a spout opening;

(d) a tubular coupling member adapted to be removably secured at one end to the end section of the spout and at its other end to an external conduit, said coupling member having an internally ribbed section at said one end with the ribs extending circumferentially around the opening through the coupling member; and (e) an externally circumferentially ribbed section on the end section of the spout for mating with the ribbed section of the coupling member to provide a fluid tight connection therebetween.

6. The appliance of claim 5 wherein:
(a) the one end of the coupling member is rigid in construction relative to said spout.

7. The appliance of claim 6 wherein:
(a) the opening through the coupling member tapers in cross-section as measured in a direction extending from the other end toward the one end thereof; and
(b) said coupling member is flexible in construction along said tapered cross-section to tightly engage the inserted end of the external conduit in sealing relationship.

8. The appliance of claim 7 wherein:
(a) the coupling member and spout are constructed of the same flexible vinyl plastic material; and
(b) the one end of the coupling member is sufficiently thick in cross-section to provide said rigid construction.

9. In a stoma drainage appliance having a pouch with upper and lower sections, the upper section being constructed of four superimposed layers of flexible material defined by two outside sheets and two inside sheets, and the lower section being constructed of two, superimposed layers of flexible material defined by extensions of said outside sheets, all of said layers being sealed to each other about their periphery to form said pouch, the lower edges of the two inside sheets extending freely across the pouch from one peripheral side edge to the other, an inlet opening in the upper section of the pouch communicating with the space between the two inside sheets and through which drainage fluid from the stoma is received, an outlet opening in the lower section of the pouch communicating with the space between the two outside sheets for draining collected fluid from said pouch, and sealing means disposed between said inlet opening and the lower edges of the two inside sheets for sealing said sheets together along a zone spaced from and extending generally along the lower edges to enable said lower edges to function as a valve deterring fluid collected in said lower section from flowing in an upward direction between said two inner sheets and into said upper section, the improvement wherein:

(a) said sealing means is defined by two spaced arcuately shaped seal lines disposed along said zone with the concave sides facing away from said inlet opening and with an unsealed space between the seal lines and an unsealed space between each seal line and the peripheral side edges of the pouch;

(b) the unsealed space between the seal lines is centrally located between the sides of the pouch directly below said inlet opening to provide a direct path between said inlet opening and the lower section of the pouch for passage of drain tubes entering said inlet opening, the convex sides of said seal lines defining arcuate guiding surfaces for guiding the drain tubes entering said inlet opening in a generally straight path through said space and into the lower section of the pouch; and (c) the seal lines unite the two inside sheets to each other.

* * * * *